Figure 1:
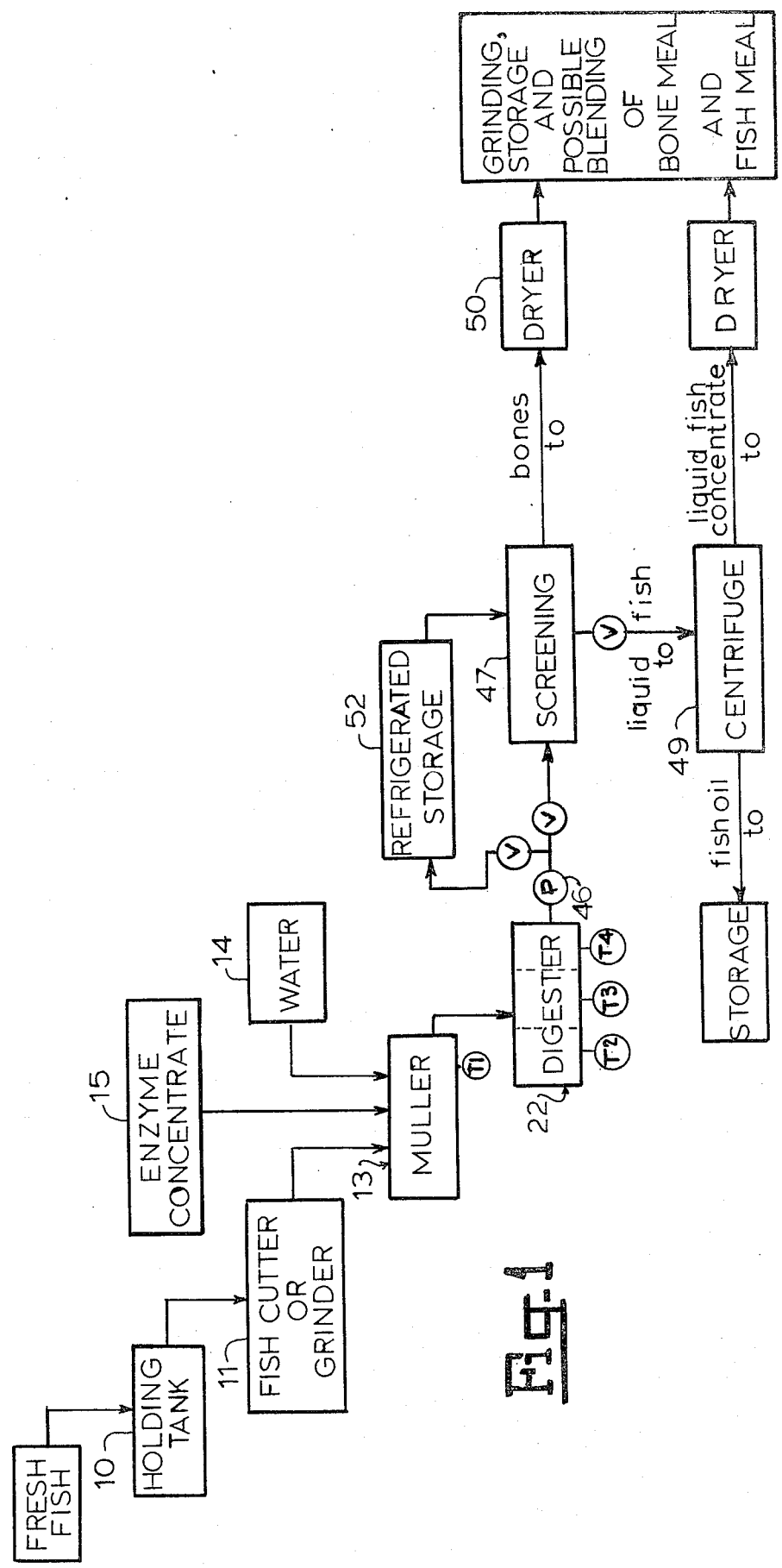

United States Patent [19]

Jeffreys et al.

[11] 4,405,649

[45] Sep. 20, 1983

[54] PROCESS FOR PRODUCING PREMIUM QUALITY FISH MEAL FROM WHOLE FISH

[75] Inventors: George A. Jeffreys; James F. Tobey, Jr.; Jean L. Price, all of Salem, Va.

[73] Assignee: Marvin Dudley, Beaumont, Tex.

[21] Appl. No.: 185,429

[22] Filed: Sep. 9, 1980

Related U.S. Application Data

[63] Continuation of Ser. No. 36,293, May 7, 1979, abandoned, which is a continuation of Ser. No. 853,532, Nov. 21, 1977, abandoned.

[51] Int. Cl.³ .............................................. C12K 1/00
[52] U.S. Cl. ........................................ 426/59; 426/7; 426/56; 426/643; 426/646; 426/807
[58] Field of Search ............... 426/7, 56, 55, 59, 643, 426/646, 807

[56] References Cited

U.S. PATENT DOCUMENTS

| | | | |
|---|---|---|---|
| 3,041,174 | 6/1962 | Ehlert | 426/7 |
| 3,170,794 | 2/1965 | Jeffreys et al. | 426/7 |
| 3,249,442 | 5/1966 | Keyes et al. | 426/7 X |
| 3,547,652 | 12/1970 | Jeffreys | 426/7 |
| 3,561,973 | 2/1971 | Rutman | 426/7 |

*Primary Examiner*—R. B. Penland
*Attorney, Agent, or Firm*—John S. Roberts, Jr.

[57] ABSTRACT

A process for producing a high quality protein fish meal from whole fish, including trash fish, either on board ship or on shore, by using an appropriate proteolytic enzyme which liquefies the fish in a digester equipped with high speed blenders, liquefying the fish by heating in the digester, pasteurizing the liquid fish so that the liquid can be stored under refrigeration for several weeks without spoilage, screening the bones out, and centrifuging part of the oil, if necessary, then drying it.

1 Claim, 3 Drawing Figures

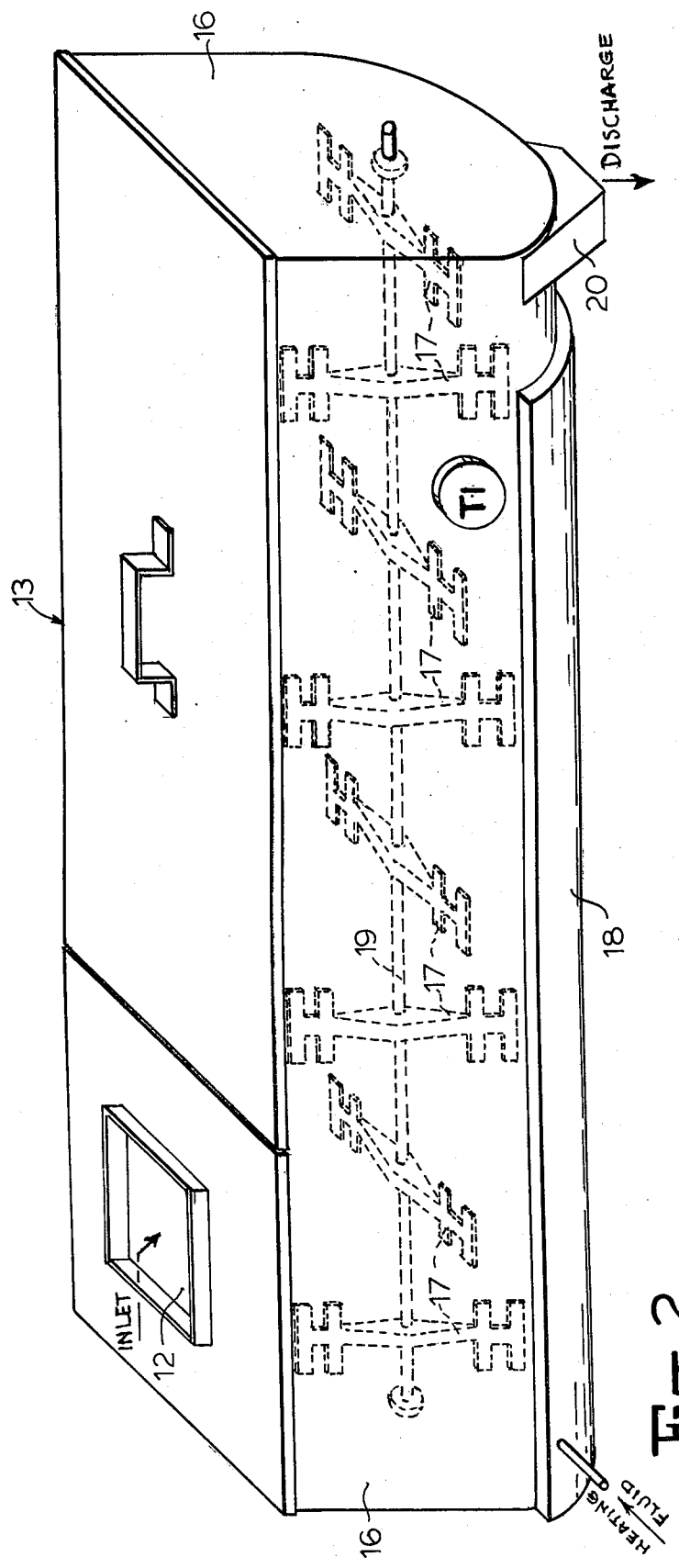

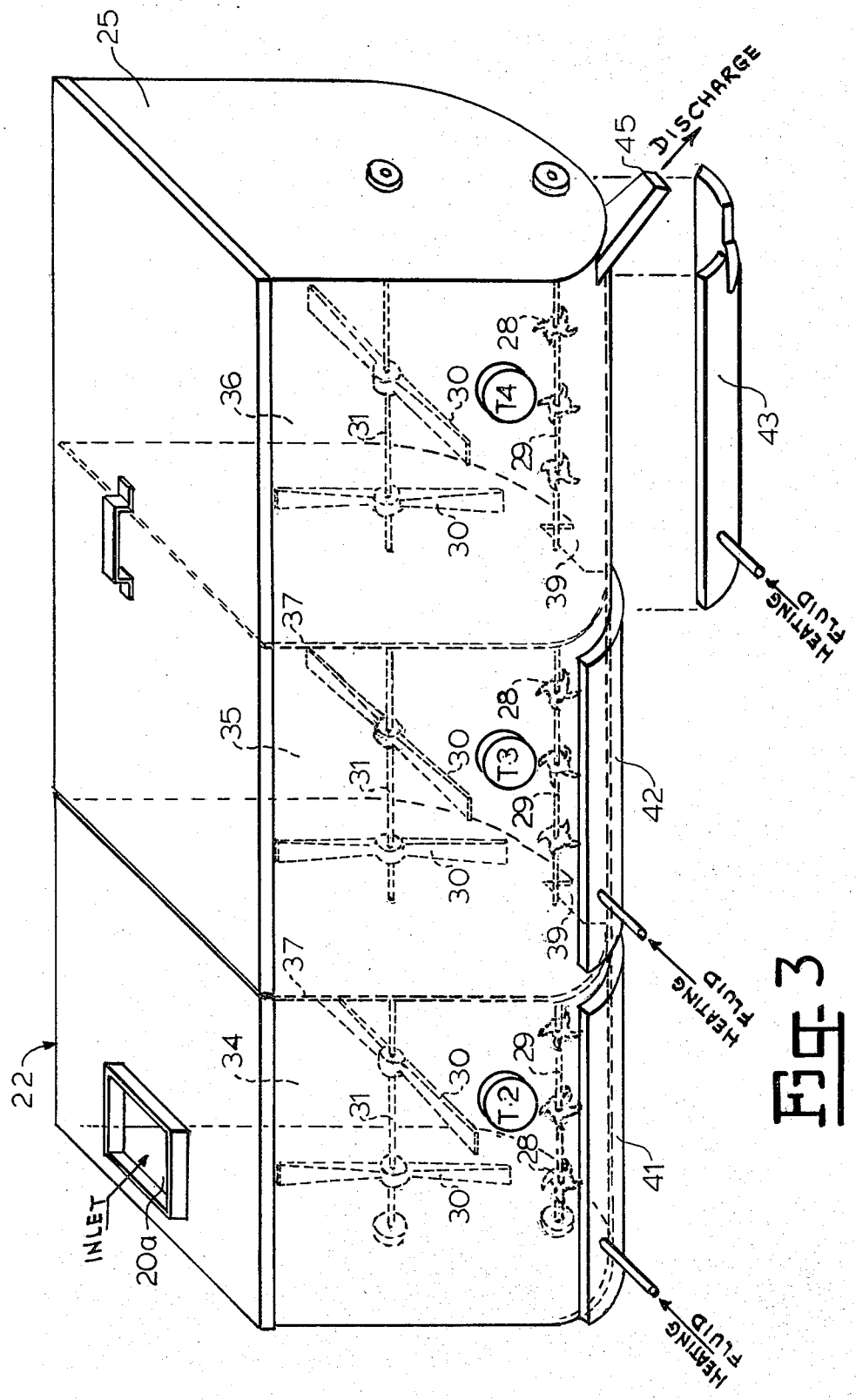

PROCESS FOR PRODUCING PREMIUM QUALITY FISH MEAL FROM WHOLE FISH

This is a continuation of application Ser. No. 036,293, filed May 7, 1979, now abandoned, which is a continuation application of Ser. No. 853,532 filed Nov. 21, 1977, now abandoned.

This invention is a process for producing a high quality protein fish meal for animal feeding and for human consumption. The process utilizes various types of fish including those species known as trash fish and other marine species suitable for food but presently not being utilized.

The Food Agriculture Organization (FAO) of the United Nations estimates that over 100 million metric tons per year of fish are not presently utilized for human or animal consumption, but instead, are wasted. Most of the fish wasted are called trash fish which are discarded because of their small size, or because of undesirably mixed varieties, or because they cannot be readily prepared for human consumption by filleting. The primary reason for not being utilized is that there are no practical methods of processing them. Still another problem involved with salvaging this type of fish by conventional means is that they must be brought to shore each day, and this makes it too costly to save them since their market value is comparatively low.

PRIOR ART

Heretofore, numerous processes have been developed in which enzymes are used for treatment of fish, but so far as applicants are aware, none have been shown to be practical for attaining the objects of the present invention, nor are any of them now in operation. Several of the prior processes employ antibiotics which are prohibited by the Federal Drug Administration as a preservative in foods, and some or both use a hydrolyte which is soluble. Some attempt to produce a hydrolysate (soluble form) which takes a long time, is expensive and not suitable for our purposes.

More particularly, U.S. Pat. No. 2,933,398 discloses a process in which an extract from meat or fish with 10% milk and Aureomycin is used to preserve fillets.

The process in U.S. Pat. No. 3,249,442 not only employs an antibiotic, but also produces a fish hydrolysate. The fish are hydrolyzed to a soluble state and the solubles as well as the solids are dried.

U.S. Pat. No. 3,697,285 discloses another process for producing a water soluble protein from fish, which process involves hydrolyzing with an enzyme, then extracting and separating the protein: but it does not produce a high quality fish meal from whole fish including the soluble fraction, not would it be practical in processing trash fish on board ship.

The fish deodorizing process in U.S. Pat. No. 3,170,794 is based on the use of a protein-modifying fungal enzyme produced by culturing the mold on a substrate of wheat bran. The enzyme is used in digesting eviscerated fish meat in the presence of yeast and sugar.

The process of U.S. Pat. No. 3,561,973 is for the production of a water soluble protein with the addition of fat. This would not produce a high quality fish meal consisting of whole fish and not just the soluble fraction. The process also involves washing and deboning steps which would not be practical or desirable on trash fish.

THE INVENTION

One objective of this invention is to render it practical to process the freshly caught fish on board ship by a series of simple steps using compact equipment, and then stored for an extended period in liquid form in refrigerated tanks on the ship. This permits the ship to remain at sea for as long as 21 days without spoilage of the fish. When the ship reaches port, the liquefied fish is pumped into storage tanks on shore for final processing, thereby providing a tremendous economical advantage over previous methods.

We have found that the fish can be liquefied easily with proper physical treatment combined with an appropriate enzyme in as little time as 15 minutes. This accelerated liquefication is effected by using relatively heat stable enzymes such as those contained in Novo's product, Alcalase, or similar enzyme products, produced from B. subtilis or othe suitable bacteria. Almost any proteolytic enzyme can be used that will liquefy animal protein and has an optional range of activity at temperatures of 30° C. to 70° C. and that functions at a pH of 4.5 to 8.0. Enzymes can be used from various sources such as: plants which yield papain and ficin; animals which furnish trypsin and pepsin; fungi such as *Aspergillus orvzae* and *Aspergillus niger;* and bacteria such as *Bacillus subtilis* and *Bacillus licheniformis*. The enzyme *B. subtilis* is preferable to many others in our process because of its relative heat stability.

The degree and length of digestion can be modified by simply increasing or decreasing the amount of enzyme producing the desired results. In our process, temperatures can easily be adjusted as required by the type of proteolytic enzyme used to produce an accelerated digestion, during which a liquid mixture of fish and enzyme is compartmentalized and progressively heated at stepped levels to at least 82° C. concurrently with vigorous agitation to effect pasteurization and to inactivate the enzymes.

At the same time, this process renders it unnecessary, or even desirable, to completely solubilize the fish proteins, but rather the protein chains should be modified into fragments that remain in a colloidal form which permits screening out the bones and scales and makes it possible to spray or drum dry it without appreciably damaging the constitutive amino acids and their nutrient value.

It should be pointed out that our process does not require the use of preservatives or antibiotics to keep the liquid fish from bacterial spoiling, but instead, simply a short time pasteurization by heat and a fast cooling of the liquid fish to a temperature slightly above freezing. When kept at this temperature, the product will keep without spoiling for as long as 21 days.

Further objects and characteristics of the invention will appear as the description proceeds when taken in connection with the accompanying drawings, in which FIG. 1 is a flow diagram of the process according to the invention;

FIG. 2 is a schematic view showing the principal components of a muller or masher employed in the process, and FIG. 3 is a schematic view showing the principal components of a digester employed in the process.

A description of the various steps of the process follows:

The fresh whole fish in holding tank 10 are conveyed at a definite rate to fish cutter 11 (FIG. 1). This cutter cuts the fish into approximately ½ inch chunks, the purpose of which is to keep the bones from being cut up too finely and to insure that the bones remain in pieces that can be screened out by suitable means such as a vibrating screen to be described later. The mass of cut-up fish is fed through inlet 12 into a muller or masher 13 (FIG. 2) along with 10 to 40% water 14 and a definite amount of enzyme concentrate 15 ranging from 0.05 to 0.2% (both based upon the weight of whole fish). The muller or masher may be a U-shaped conveyor-type vessel 16 equipped with rotating paddles or flights 17, which paddles mash and mix the fish with the enzymes as it travels along. Vessel 16 is equipped with a steam or hot water jacket 18 that heats the fish from 50° to 57° C. by the time it is discharged as at 20 into a digester 22. The temperature in muller 13 is regulated by a thermostat T1 located near the discharge end 20. The length of vessel 16 is determined by the capacity and residence time desired. Usually, the capacity of the muller 13 is about ⅓ the volume of digester 22, the residence time in the former being between 5 and 10 minutes. After passing through the muller, the blended and warmed fish is next dropped into the digester 22 at its inlet 20a.

The digester 22 may be a stainless steel vessel 25 (FIG. 3) of similar construction as the muller but three times larger. The capacity of the digester is determined by the amount of fish to be processed per hour. We have found that a 1-gallon capacity digester will continuously process 17.5 lbs. of fish per hour including the added water. Hence, a pilot model of 8 gallons will continuously process 140 pounds fish per hour; and a full scale digester of 457 gallons will liquefy 8000 pounds or four tons per hour.

In order to promote intimate contact between the enzyme and the fish flesh, a series of small blending blades 28 are provided within the digester, said blades being mounted on a horizontally disposed rotatable shaft 29 extending lengthwise and close to the bottom of the vessel 25. These blades are adapted to rotate at high speed, blending the enzyme with the fish while rubbing the flesh off the bones. Located above blades 28 are slowly rotating mixing paddles 30 mounted on shaft 31, said paddles keep the lighter particles in suspension as the heavier particles sink toward the bottom in the zone of vigorous agitation. Thus, the small high-speed blenders 28 disintegrate and accelerate liquefaction. Time required for digestion without such vigorous agitation can be as long as four hours; as compared with a residence time as little as 15 minutes using the digester described above.

The digester 22 is divided into three equal sections or compartments 34, 35 and 36 by partitions 37, 37, which partitions extend to the bottom leaving an opening or passageway 39 in each for the fish mixture to pass from one compartment to the other. Compartments 34, 35 and 36 are individually heated by steam jackets 41, 42 and 43 respectively, and the respective temperatures are controlled by thermostats T2, T3 and T4 each located at the mid-point of a compartment. As shown in the flow diagram (FIG. 1), the movement of the fish is determined by the continuous amount being fed at the head end or inlet of the digester. A comparable amount is discharged at the opposite end 45 by means of a positive acting sludge pump 46. The temperature of the first section 34 is maintained between 50° and 57° C.; the temperature of the middle section 35 is maintained between 60° and 65° C.; and the third or last section 36 is allowed to reach 82° to 87° C. The 82-degree temperature pasteurizes the liquid and inactivates the naturally occurring and supplemented enzymes.

The hot liquid fish is discharged continuously by the aforementioned pump 46 onto a vibrating screen which may be of any suitable mesh from #6 to as high as #20. Preferably, a #10 screen is used which would provide suitable separation of the bones and scales.

If the fish contains a high percentage of fat or oil, most of the oil can be removed after the bones are screened out by centrifuging as at 49. For practical purposes, the amount of oil in the dried meal is limited to a range of from 2 to 10%. Some fat is desirable for animal feed for which the average should remain about 6%.

After oil separation, the liquid fish is combined with the solids and sludge obtained from centrifugation. A suitable antioxidant is added to prevent rancidity in the residual oil which will be combined in the dried product. Examples of suitable antioxidants are: Butylated Hydroxytoluene, Butylated Hydroxyanisole, Ethoxyquin, and x-tocopherol, or mixtures thereof.

It should be pointed out that fish with low fat content of 2 to 3% need not be subjected to centrifugation. The fat content of the final dry product should not be over 12%.

When fish is to be processed on board ship, the bones may be left in or screened out during this stage of processing. If the bones are screened out, a simple continuous dryer 50 would be used to dry the bones. This both possible and practical aboard ship. If the bones are left in, the storage tanks should be constructed in such a way that permits the bones to be easily stirred and discharged. For example, the tanks may be provided with a U-shaped bottom equipped with a slow mixing rotor mixer, otherwise the bones will have a tendency to settle to the bottom and clog the discharge pump.

The final temperature of 82° C. in compartment 36 of the digester is sufficient to kill off *Escherichia coli*, Salmonellae and other nonspore-forming microorganisms. Antioxidants are added before cooling. The hot liquid fish should be cooled down to 2° C. as fast as possible (in 3 hours or less). This can be achieved economically by using sea water as a coolant in the first stage, and then using refrigerated brine in the final stage to bring the fish to 2° C. or less. The cooled liquid fish is pumped into refrigerated holding tanks. Our tests have shown that fish cooled and stored in the above manner will keep as long as 21 days. When the ship reaches shore, the liquefied fish is pumped into refrigerated tanks on shore, and then processed in the following manner: The liquid fish is first heated to 71° C. or higher. If the bones have been previously screened out, the liquid is centrifuged if necessary to remove excess oil. The liquid fish is then dried by spray drying, drum drying or vacuum drying.

The screened bones in all cases may be dried separately in a simple rotary hot air dryer. If desired, the bones may be ground and recombined with the final dried fish meal in any proportions desired.

In order to more clearly describe the nature of the present invention, specific examples will hereinafter be described. It should be understood, however, that this is done solely by way of example and is intended neither to delineate the scope of the invention nor limit the ambit of the appended claims. The process could be achieved in a batchwise fashion or steps; however, the continuous process provides distinctly more economical advantages. In the examples and throughout the specification, percentages refer to percent by weight unless otherwise specified. The temperatures used are Centigrade.

EXAMPLE I

A pilot model was used in this example. The capacity of the digester was 8.2 gallons. This digester allowed the processing of 140 pounds of fish per hour with residence time of 20 minutes in the digester itself. Eight gallons capacity will hold about 46½ pounds of fish including the added water. The muller had a capacity of 2.7 gallons and provided a residence time of about 5 minutes.

Cut fish in ½ inch chunks was fed into the muller through a feeder at a rate of 2⅓ pounds per minute. At the same time, the enzyme concentrate, Alcalase 1.5 P, was fed dry by a percentage feeder at 1.05 grams/minute or at 0.1% level based on the input of ground fish. Water was added with the enzyme through a flow meter at the rate of 354 ml. per minute, or at 30% level. Heat was applied through the jacket of the muller and internal temperature was maintained at 55° C. The speed of the mulling flights was set at 70 RPM. At the end of 5 minutes, the mulled fish began to discharge into the digester at a temperature of 55° C. The digester was allowed to fill for about five minutes until the mixture covered the high-speed blending propellers, and the temperature in all sections or compartments was kept between 55° and 57° C. during this time. The rotation of the high-speed blending blades at 500 RPM was then started and this immediately started to liquefy the fish. When the digester became half full, the slow mixing paddles were started at a rate of 40 RPM. The temperature of the middle section was regulated at 60° C. and the discharging end section remained at 87° C. Equilibrium was reached after 25 minutes and the liquid fish began discharging. (See FIG. 3).

The temperature in all sections 34, 35 and 36 were constantly maintained at the required levels being: 55° to 57° C. in the first section, 60° to 65° C. in the second, and 82° to 87° C. in the last. The liquid fish was continually discharged by pump 46 into a vibrating sifter 47 equipped with a No. 10 screen (FIG. 1). The bones were easily sifted out and discharged on one side and the liquid was discharged through the bottom spout. Before the bones were discharged, they were sprayed with a small amount of hot water, approximately 2% based on the fish. This amount of added water is not critical but produces cleaner bones, thus obtaining more efficient separation of the proteinaceous fraction of fish from the bones.

At the end of two hours, 284 pounds of fish had been processed into a liquid state having approximately 17.5% solids. Approximately 12 pounds of bones were recovered (on a dry basis) from the above volume of fish. The bones were then dried in a conventional dryer.

The liquid fish was immediately cooled to 2° C. and divided into three portions labelled A, B and C. A and B were placed in containers for storage at 1° to 2° C. Portion C was immediately dried at 57° C. in a 150" film on metal trays. After 15 days storage, to check characteristics of the fish after storage, portion A was spray dried, and portion B was drum dried.

Following are the Protein Efficiency Ratio (PER) results of the 3 portions FFC mentioned in Example #1. Per is a method of testing the quality of a protein by the growth rate obtained on rate when fed as a sole source of protein as compared to casein.

The three portions of the dried samples were assayed by Wisconsin Alumni Research Foundation (WARF) for Protein Efficiency Ratio (PER). These were as follows based on standard casein rated as 2.5: Sample A-Spray Dried-2.40; Sample B-Drum Dried-2.44; and Sample C-Lab Dried-2.71.

The average of the 3 samples was 2.51. These results compared to commercial fish meal on the market was 2.2 and soybean meal 1.9. The results indicate that the FFC was equal to casein and superior to commercial products.

EXAMPLE II

This test was performed in identical manner to that in Example I with the additional step of removing part of the oil by centrifugation. After removing the bones, the hot liquid fish was passed through a continuous discharge centrifuge 49. Before centrifuging, the oil content was 20% and the protein content was 67%. Centrifugation removed a large part of the oil so that the dried product upon assay was found to contain 9.30% oil and 73.85% protein. Before drying the liquid fish, 0.025% antioxidant was added.

EXAMPLE III

The process was repeated as in Example I except the enzyme from plant source, Ficin, was used at the level of 0.025%. The temperatures in the digester were 5 degrees lower in the first two sections, that is, in the first section 45° to 50° C., in the second section 55° to 60° C., and in the last section 75° to 85° C. which remained substantially the same. The process was then completed as in Example I.

We claim:
1. A continuous process for producing a liquefied intermediate for protein fish meal comprising mixing and mashing comminuted whole fish with water and a proteolytic protein liquefying enzyme used at pH parameter of 4.5–8.0 and a temperature parameter of 30°–87° C. forming an aqueous mixture, vigorously agitating the lower portion of the aqueous mixture to reduce the mixture to flesh and bone particles and concurrently agitating the upper portion of said mixture at a relatively slow rate to maintain the lighter particles in suspension while the heavier particles sink to said lower portion and further compartmentalizing said aqueous mixture into multiple closed compartments while agitating and liquefying said comminuted fish at progressively increasing and controlled temperatures in each of said closed compartments.

* * * * *